United States Patent [19]

Schmitt

[11] 4,370,146

[45] Jan. 25, 1983

[54] INFRARED ABSORPTION DETERMINATION OF SULFONATE SURFACTANTS UTILIZING DEUTERATED SULFONATES

[75] Inventor: Kirk D. Schmitt, Pennington, N.J.

[73] Assignee: Mobil Oil Corporation, New York, N.Y.

[21] Appl. No.: 331,056

[22] Filed: Dec. 16, 1981

[51] Int. Cl.$^3$ .................... G01N 21/35; E21B 47/00; E21B 49/08

[52] U.S. Cl. .................. 436/120; 166/252; 436/30

[58] Field of Search .............. 23/230.3, 230 R; 166/250, 252

[56] References Cited

U.S. PATENT DOCUMENTS

| | | | |
|---|---|---|---|
| 3,480,080 | 11/1969 | Murphy | 166/252 |
| 3,500,912 | 3/1970 | Davis | 166/252 |
| 3,969,076 | 7/1976 | Wang | 23/230 R |
| 3,992,149 | 11/1976 | Wang | 23/230 R |
| 3,993,131 | 11/1976 | Riedel | 166/252 |
| 4,088,189 | 5/1978 | Shupe | 166/252 X |
| 4,168,746 | 9/1979 | Sheely | 166/252 |
| 4,203,491 | 5/1980 | Reisberg | 166/252 X |
| 4,258,789 | 3/1981 | Hedges | 166/252 |
| 4,278,128 | 7/1981 | Satter | 166/250 |
| 4,299,711 | 11/1981 | Tyler | 166/252 X |

OTHER PUBLICATIONS

D. M. Clementz, Anal. Chem., 49(8), 1148–1152, (Jul. 1977).

Chemical Abstracts, 85:10199r, (1976).

*Primary Examiner*—Sidney Marantz
*Attorney, Agent, or Firm*—Charles A. Huggett; Michael G. Gilman; Edward F. Kenehan, Jr.

[57] ABSTRACT

A method for determining the concentration of a brine tolerant sulfonate surfactant in a complex mixture containing, in addition to said brine tolerant sulfonate surfactant, lignosulfonates, crude oil, salts, and water and, optionally, petroleum sulfonates and alcohols, that comprises incorporating into the brine tolerant sulfonate surfactant molecule a small amount of deuterium prior to addition to the complex mixture and determining the concentration of the brine tolerant sulfonate surfactant by measuring its infrared absorption at 2150 cm$^{-1}$.

2 Claims, No Drawings

INFRARED ABSORPTION DETERMINATION OF SULFONATE SURFACTANTS UTILIZING DEUTERATED SULFONATES

BACKGROUND OF THE INVENTION

1. Field of the Invention

This inventon is concerned with a method for determining the concentration of brine tolerant surfactants in complex water flood mixtures.

2. Description of the Prior Art

The existence of an infrared absorption due to the deuterium isotope of hydrogen is well known.

Deuterium labelling has been used as a probe to determine the molecular mechanisms of reactions. In such use, the goals have been to determine if the deuterium has remained in the molecule and, if so, where in the molecule it may be found.

Insofar as is now known, the incorporation of deuterium in a brine tolerant surfactant molecule to allow selective detection and determination of small amounts of the surfactant in a complex mixture has not been proposed.

SUMMARY OF THE INVENTION

This invention provides a method for determining the concentration of a brine tolerant sulfonate surfactant in a complex mixture containing, in addition to said brine tolerant sulfonate surfactant, lignosulfonates, crude oil, salts, and water and, optionally, petroleum sulfonates and alcohols, that comprises incorporating into the brine tolerant sulfonate surfactant molecule a small amount of deuterium prior to addition to the complex mixture and determining the concentration of the brine tolerant sulfonate surfactant by measuring its absorption of infrared light at about 2150 cm$^{-1}$.

DESCRIPTION OF SPECIFIC EMBODIMENTS

The brine tolerant sulfonate surfactants contemplated herein are compounds having the formula R-(OC$_2$H$_4$)$_n$-OCH$_2$CH$_2$CH$_2$SO$_3$M, wherein R is alkyl having between about 10 carbon atoms and about 30 carbon atoms, n is 2-6, and M is an alkali metal. When the R group is a straight, i.e., normal, chain a cosurfactant must be used, e.g., an alkanol.

A preferred class of brine tolerant sulfonate surfactants is disclosed in copending application Ser. No. 259,216, filed Apr. 30, 1981, which is incorporated herein in its entirety by reference. That application describes surfactants in which R is branched chain, i.e., two-tailed. These brine tolerant surfactants are effective at low concentrations, between about 0.001 weight percent and about one weight percent.

In order to optimize the performance of these brine tolerant surfactants in low tension waterflood operations, it is necessary to know the concentration of the brine tolerant surfactant. These surfactants are expensive components of enhanced oil recovery fluids and it is important that neither too much nor too little surfactant will be used.

Standard methods of analysis for surfactants, such as dye titration, are adequate for simple fluids containing a single sulfonate, but fail in complex systems because they are nonselective and give only total sulfonate concentrations. Methods based on high pressure liquid chromatographic separation fail for several reasons. There may be no way to separate the brine tolerant surfactant from the other components or the brine tolerant surfactant may not have a sufficiently strong UV chromaphore to render its easy detection by UV. The low concentration of surfactant in produced fluids makes impractical other high pressure liquid chromatographic detection techniques, such as refractive index or electrochemistry.

The synthetic procedures for incorporating deuterium into organic molecules are well known. They include reduction of double or triple bonds by deuterium-containing hydrogen gas over heterogeneous catalysts; scrambling of carbon-hydrogen bonds over similar catalysts; reduction of carbonyl or other unsaturated functional groups by deuterium-containing hydrides; acid catalyzed exchange of deuterium for hydrogen on aromatic rings; and base catalyzed exchange of deuterium for hydrogen on acidic carbons. The particular method used to incorporate deuterium into the brine tolerant surfactant molecule is not a critical factor in the method of this invention.

The brine tolerant surfactants are expensive components of enhanced oil recovery fluids used in waterflood operations. In addition, other components are often present in aqueous oil recovery fluids including sacrificial agents, such as petroleum sulfonates and lignosulfonates; thickeners, such as polymers; cosurfactants, such as alcohols used when R is straight chain alkyl; brine components, such as sodium chloride, calcium chloride, and magnesium chloride; and crude oil.

No component of such a complex mixture absorbs infrared light at about 2150 cm$^{-1}$ except the deuterium labelled brine tolerant surfactant and water which can be removed by evaporation.

EXAMPLE

The surfactant was synthesized conventionally according to Scheme I. Deuterium was introduced in three different locations to illustrate the ease with which it can be incorporated.

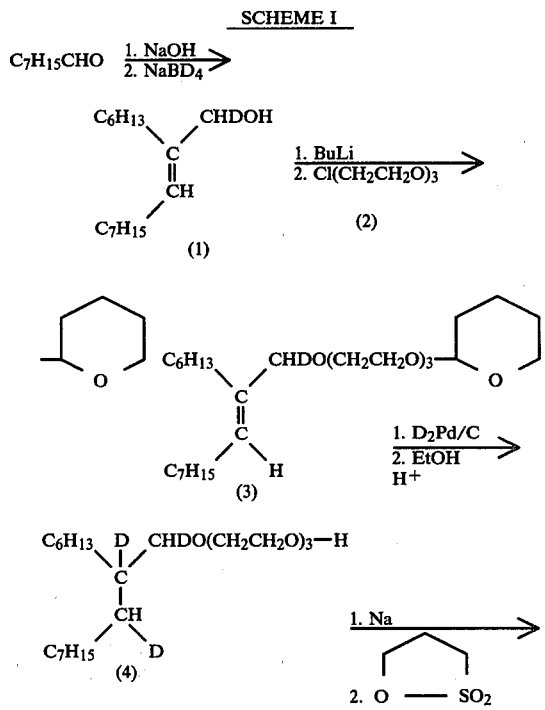

SCHEME I

-continued
SCHEME I

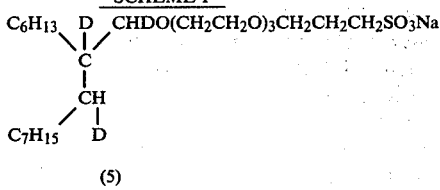

(5)

Thus, 177 g. octanal and 250 ml. 95% ethanol were refluxed and 25 ml. 3 N NaOH added over 15 minutes. After 20 minutes at reflux, the mixture was cooled to 15° C. and 8.3 g. NaBD$_4$ in 70 ml. 0.22 N NaOH plus 180 ml. ethanol added in 20 minutes. After workup and distillation at 113°–119° C./0.05 mm. Hg, 118 g. of a white oil were obtained whose carbon-13 NMR showed incorporation of deuterium in the alcohol carbon of compound (1) by virtue of a 1:1:1 splitting of 21.5 Hz. This 117 g. alcohol (1) were dissolved in 360 ml. xylene, degassed via several cycles of a Firestone valve, dried by azeotropic removal of water, cooled to 15° C. and 320 ml. 1.5 M BuLi in hexane added over 30 minutes. The hexane was distilled out to give a pot temperature of 144° C. and 136.6 g. tetrahydropyran protected chloride (2) added all at once. After four hours at reflux, the mixture was worked up, the low boiling materials distilled out, and the crude residue (3) treated in 46 g. portions with 92 ml. ethyl acetate and 2.12 g. 10% palladium on charcoal catalyst under 50 psig. deuterium in a Parr shaker for eight hours. After filtration and removal of solvent, the tetrahydropyran protecting group was removed by 1 hour reflux with 570 ml. ethanol and 31.5 g. pyridinium p-toluenesulfonate. After workup and Kugelrohr distillation at 175°–185° C./0.1 mm. Hg., 80.5 g. pale yellow alcohol (4) were obtained. Deuterium NMR indicated three deuteriums per molecule had been incorporated but carbon-13 NMR showed some scrambling to have taken place by virtue of the fact that the carbons at 38.3 ppm and 31.5 were not completely converted to 22 Hz 1:1:1 triplets. Alcohol (4) shows an intense absorption at 2153 cm$^{-1}$ in the infrared. It was converted to brine tolerant surfactant (5) by refluxing the 80.5 g. in 280 ml. dry toluene with 4.62 g. sodium until all the sodium dissolved, cooling to 25° C., and adding 24.7 g. propane sultone. After evaporation of solvent recrystallization from acetone/water gave 82.4 g. white wax whose carbon-13 NMR was completely consistent with its structure and which showed a strong carbon-deuterium stretch in the infrared spectrum at 2151 cm$^{-1}$.

Analyses of complex mixtures containing oil, surfactant, petroleum sulfonate, lingno-sulfonate, salt, and water can be obtained by centrifuging most of the bulk oil and evaporating the water. The residue may be analyzed directly as a KBr pellet or by redissolving the sample in chloroform. Surfactant in oil may be obtained directly by obtaining the infrared spectrum of the oil, neat or in solvent, in a solution cell. Analysis for one of two or more brine tolerant surfactants can be easily carried out by this method if the surfactant of interest alone is labelled.

As an example of one way in which the analysis might be carried out, a series of solutions each containing 1% ERA-16, a ligno-sulfonate from American Can Corporation, varying amounts of deuterated surfactant (5), water, and 6% salt consisting of NaCl, CaCl$_2$ and MgCl$_2$ in ratio by weight 4.75%:0.90%:0.34% were shaken with crude oil, centrifuged, evaporated, and the residue taken up in chloroform and filtered from insoluble salts. The infrared absorbance of 2150 cm$^{-1}$ was determined using a standard solution cell and a Nicolet 7199 infrared spectrometer. The measurement time for the spectrometer was one minute 30 seconds. The concentration was determined by comparison of the absorbance measured to the absorbance of known solutions of surfactant (5).

Table 1 compares the known concentrations with the results found by the analysis.

TABLE 1

| Concentration of Surfactant (5) Found by IR Analysis (ppm) | Known Concentrations of Surfactant (5) (ppm) |
| --- | --- |
| 100 | 110 |
| 690 | 750 |
| 1520 | 1500 |
| 2390 | 2500 |
| 2920 | 3000 |

The method gives precise, accurate results over a range of concentrations from 100 to 3000 ppm (0.01 to 0.30%). Obviously by diluting or concentrating the solutions the effective range could be extended from 1 ppm to 100 percent.

The example illustrates the utility of the method in one of the most difficult analytical systems, namely, a brine tolerant surfactant which contains no UV detectable functionality. It shows that the surfactant can be quantified easily at levels as low as 100 ppm in the presence of high concentrations of typical surfacant solution components.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for determining the concentration of a brine tolerant sulfonate surfactant in a complex mixture containing, in addition to said brine tolerant sulfonate surfactant, lignosulfonates, crude oil, salts, and water and, optionally, petroleum sulfonates and alcohols, that comprises incorporating into the brine tolerant sulfonate surfactant molecule a small amount of deuterium prior to addition to the complex mixture and determining the concentration of the brine tolerant sulfonate surfactant by measuring its absorption of infrared light at about 2150 cm$^{-1}$.

2. The method of claim 1, wherein said complex mixture contains in a 6% brine a ligno-sulfonate, crude oil, and a deuterated surfactant having the formula:

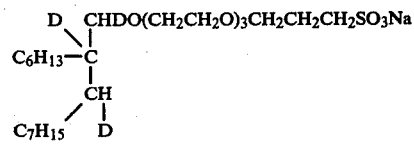

* * * * *